(12) United States Patent
Takasaki

(10) Patent No.: US 8,197,137 B2
(45) Date of Patent: Jun. 12, 2012

(54) X-RAY IMAGING APPARATUS AND CONTROL METHOD THEREFOR

(75) Inventor: Takashi Takasaki, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 234 days.

(21) Appl. No.: 12/756,454

(22) Filed: Apr. 8, 2010

(65) Prior Publication Data

US 2010/0266098 A1 Oct. 21, 2010

(30) Foreign Application Priority Data

Apr. 16, 2009 (JP) ................................. 2009-100373

(51) Int. Cl.
*G01D 18/00* (2006.01)
(52) U.S. Cl. ....................................... 378/207; 378/145
(58) Field of Classification Search .................... 378/62, 378/207, 145, 108
See application file for complete search history.

(56) References Cited

U.S. PATENT DOCUMENTS

| 6,222,906 B1 | 4/2001 | Sakaguchi et al. ........... 378/98.8 |
| 6,549,609 B1 | 4/2003 | Iinuma et al. ................. 378/150 |
| 7,494,276 B2 * | 2/2009 | Borgmann et al. ........... 378/207 |
| 2002/0122534 A1 * | 9/2002 | Polkus et al. .................. 378/205 |
| 2003/0007675 A1 | 1/2003 | Schmidt et al. ................ 382/132 |
| 2006/0056592 A1 * | 3/2006 | Tamegai ......................... 378/97 |
| 2009/0103685 A1 * | 4/2009 | Abe et al. ....................... 378/147 |

FOREIGN PATENT DOCUMENTS

| DE | 101306 1 1 A | 1/2003 |
| JP | 11-318877 | 11/1999 |
| JP | 2001-104299 | 4/2001 |
| JP | 2001-292992 | 10/2001 |

\* cited by examiner

*Primary Examiner* — Hoon Song
(74) *Attorney, Agent, or Firm* — Fitzpatrick, Cella, Harper & Scinto

(57) ABSTRACT

An X-ray imaging apparatus suppresses X-ray irradiation outside an X-ray detection unit. An X-ray imaging apparatus according to this invention includes an X-ray irradiation unit which irradiates an object with X-rays, an X-ray detection unit movably provided with an imaging unit, a first irradiation field prediction unit which calculates an irradiation field by using the relative positional relationship between generation unit and imaging unit and aperture value of a collimator, a second irradiation field prediction unit which calculates an irradiation field based on the dose of X-rays generated by the generation unit and the X-ray dose distribution detected by the imaging unit, and a predicted irradiation field decision unit which decides, as a predicted irradiation field, a region including one or both of irradiation fields respectively calculated by the first and second irradiation field prediction units.

8 Claims, 15 Drawing Sheets

FIG. 7A

| TIME (min.) S1 | CERTAINTY FACTOR DECREASE F11 (S1) |
|---|---|
| ~2 | 0.0 |
| ~4 | 0.1 |
| ~6 | 0.2 |
| ~8 | 0.3 |
| ~10 | 0.4 |
| ~12 | 0.5 |
| ~14 | 0.6 |
| ~16 | 0.7 |
| ~18 | 0.8 |
| ~20 | 0.9 |
| ~∞ | 1.0 |

FIG. 7B

| ANGLE (deg.) $\alpha$ (S1) | CERTAINTY FACTOR DECREASE F12($\alpha$(S1)) |
|---|---|
| ~2 | 0.0 |
| ~5 | 0.02 |
| ~10 | 0.04 |
| ~15 | 0.07 |
| ~20 | 0.10 |
| ~25 | 0.13 |
| ~30 | 0.17 |
| ~35 | 0.21 |
| ~40 | 0.28 |
| ~45 | 0.37 |
| ~50 | 0.49 |
| ~55 | 0.68 |
| ~58 | 0.85 |
| ~90 | 1.00 |

FIG. 7C

| MOVING DISTANCE (n) R (S1) | CERTAINTY FACTOR DECREASE F13 (R (S1)) |
|---|---|
| ~0.5 | 0.0 |
| ~1.0 | 0.1 |
| ~1.5 | 0.2 |
| ~2.0 | 0.3 |
| ~2.5 | 0.4 |
| ~3.0 | 0.5 |
| ~3.5 | 0.6 |
| ~4.0 | 0.7 |
| ~4.5 | 0.8 |
| ~5.0 | 0.9 |
| ~∞ | 1.0 |

FIG. 9A

| DOSE (μR)<br>H (S1) | CERTAINTY<br>FACTOR DECREASE<br>F21 (H (S1)) |
|---|---|
| ~ 0.2 | 1 |
| ~ 0.5 | 0.9 |
| ~ 0.9 | 0.8 |
| ~ 1.3 | 0.7 |
| ~ 2.0 | 0.6 |
| ~ 3.2 | 0.5 |
| ~ 5.0 | 0.4 |
| ~ 8.0 | 0.3 |
| ~ 12.6 | 0.2 |
| ~ 20.0 | 0.1 |
| ~∞ | 0 |

FIG. 9B

| REGION<br>B (S1) | CERTAINTY<br>FACTOR DECREASE<br>F22 (B (S1)) |
|---|---|
| CRANIAL BONE | 0.5 |
| CHEST REGION | 1.0 |
| ABDOMINAL REGION | 1.0 |
| SPINE | 0.8 |
| THORACAL REGION | 0.6 |
| PELVIS REGION | 0.4 |
| UPPER LIMB | 0.1 |
| LOWER LIMB | 0.2 |

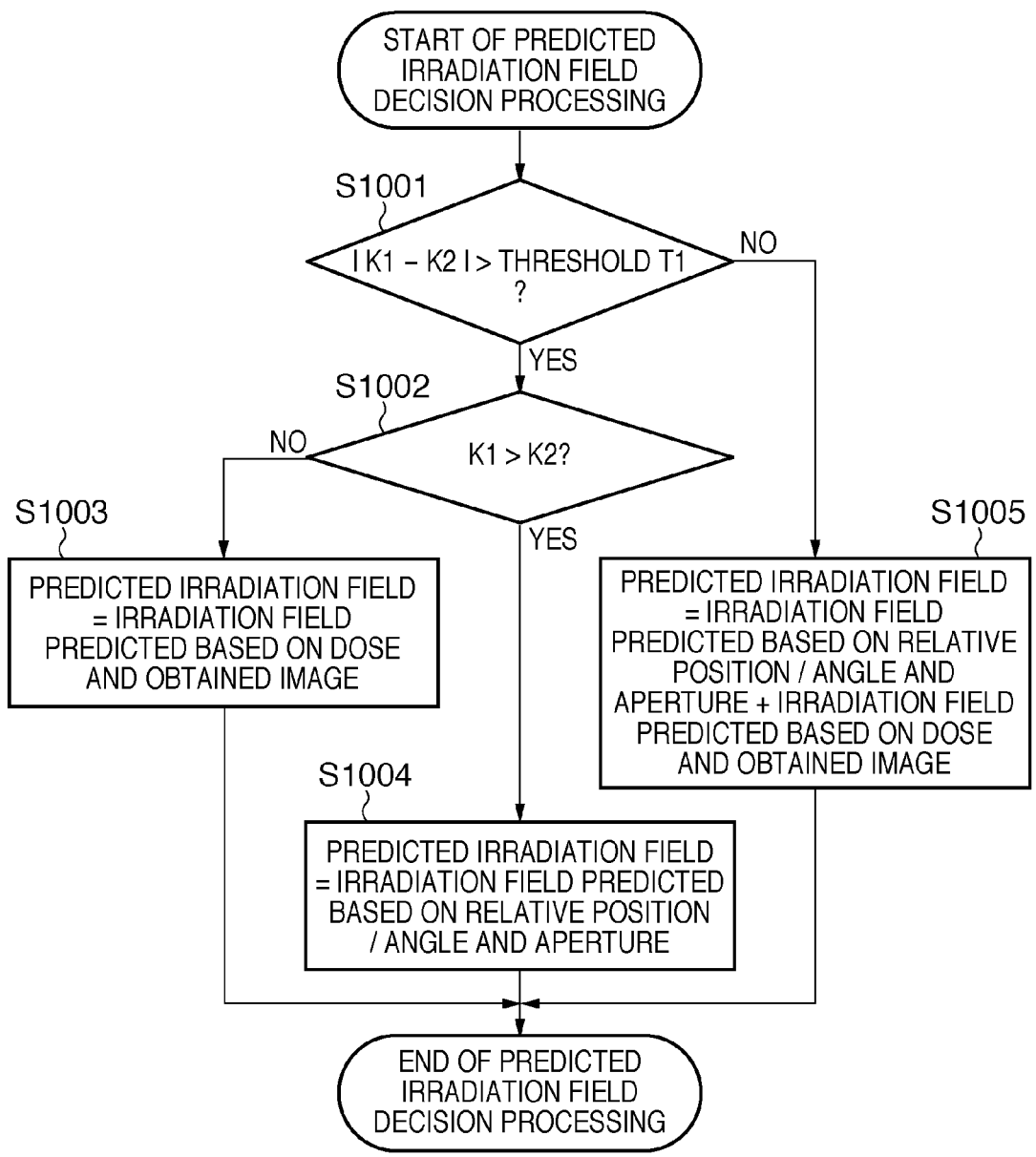

| | |
|---|---|
| S1 [min.] | 5 |
| α (S1) [deg.] | 4 |
| R (S1) [m] | 1 |
| H (S1) [μR] | 10 |
| B (S1) | PELVIS REGION |
| F11 (S1) | 0.2 |
| F12 (α (S1)) | 0.02 |
| F13 (R (S1)) | 0.1 |
| F21 (H (S1)) | 0.2 |
| F22 (B (S1)) | 0.4 |
| K1 | 0.68 |
| K2 | 0.92 |
| T1 | 0.1 |
| DETERMINATION | IRRADIATION FIELD BASED ON DOSE AND OBTAINED IMAGE |

FIG. 13

| | |
|---|---|
| S1 [min.] | 3 |
| α (S1) [deg.] | 1 |
| R (S1) [m] | 0.4 |
| H (S1) [μR] | 3 |
| B (S1) | ABDOMINAL REGION |
| F11 (S1) | 0.1 |
| F12 (α (S1)) | 0 |
| F13 (R (S1)) | 0 |
| F21 (H (S1)) | 0.5 |
| F22 (B (S1)) | 1 |
| K1 | 0.9 |
| K2 | 0.5 |
| T1 | 0.1 |
| DETERMINATION | IRRADIATION FIELD BASED ON RELATIVE POSITION / ANGLE AND APERTURE |

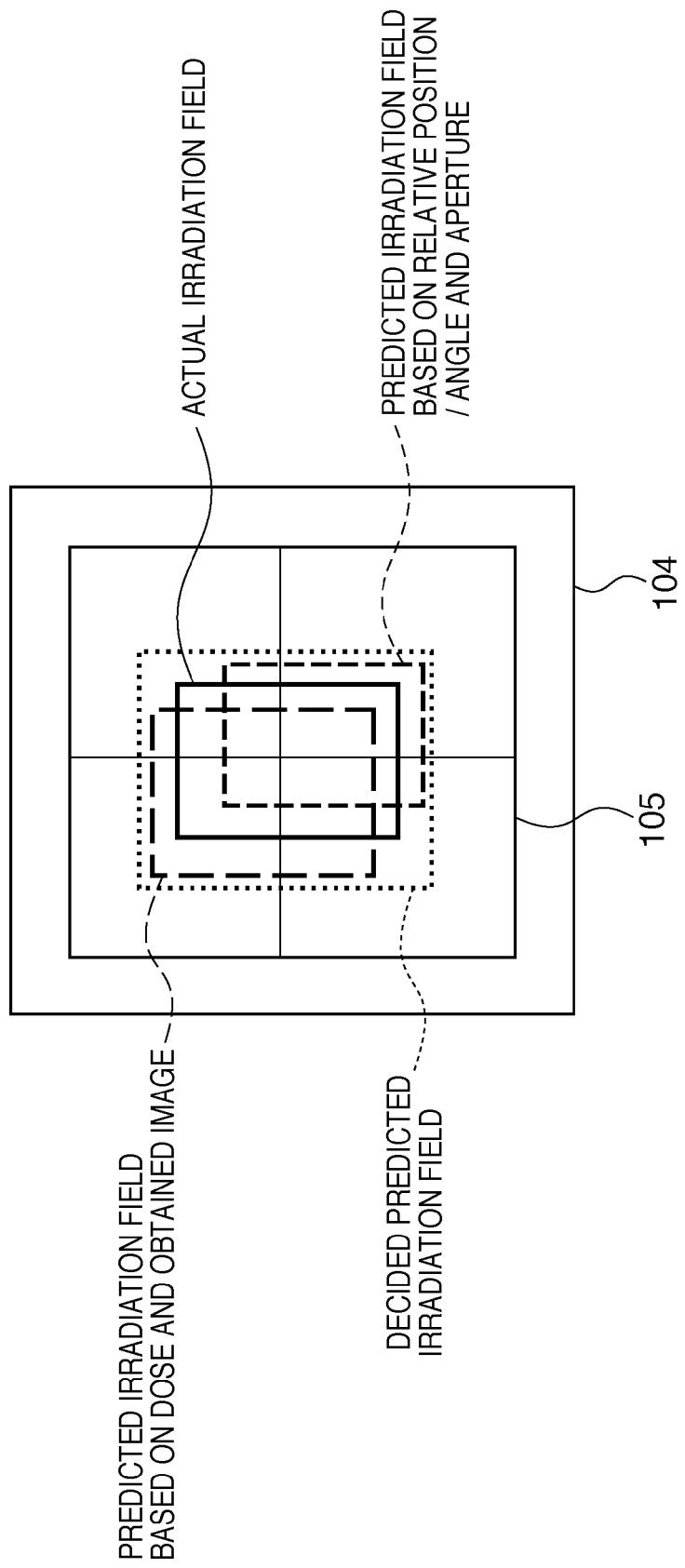

X-RAY IMAGING APPARATUS AND CONTROL METHOD THEREFOR

BACKGROUND OF THE INVENTION

1. Field of the Invention

The present invention relates to an X-ray imaging apparatus and a control method for the apparatus.

2. Description of the Related Art

Conventionally, in the medical field, X-ray imaging apparatuses have been widely used to obtain fluoroscopic images. An X-ray imaging apparatus generally includes an X-ray irradiation unit, an X-ray detection unit, and a control processing unit. Controlling the aperture of the collimator provided for the X-ray irradiation unit makes it possible to change the spread angle of an X-ray beam. It is also possible to change the relative position between the X-ray irradiation unit and imaging unit provided in the X-ray detection unit.

More specifically, it is possible to change the position and angle of the X-ray irradiation unit and the position and angle of the imaging unit provided in the X-ray detection unit. This allows the operator to change the irradiation position and irradiation direction of X-rays in accordance with purposes.

The X-ray imaging apparatus capable of changing the spread angle, irradiation position, and irradiation direction of an X-ray beam in this manner may irradiate a region other than the imaging unit of the X-ray detection unit or a region outside the X-ray detection unit. In this case, if X-rays irradiate a region other than the imaging unit of the X-ray detection unit, an object (usually part of the body of a patient) undergoes ineffective exposure. In addition, if X-rays irradiate a region outside the X-ray detection unit, the operator and surrounding people are exposed to X-rays. For this reason, such an X-ray imaging apparatus is required to minimize X-ray irradiation outside the X-ray detection unit. There have been proposed various methods for this purpose.

For example, Japanese Patent Laid-Open No. 11-318877 has proposed a method of predicting an X-ray irradiation field by acquiring the relative position information of an X-ray irradiation unit and imaging unit and the aperture information of a collimator. According to this reference, if a predicted irradiation field includes a region other than the imaging unit, X-ray irradiation outside the X-ray detection unit is suppressed by restricting irradiation and issuing a warning to the operator.

In addition, Japanese Patent Laid-Open No. 2001-104299 has proposed an arrangement including an X-ray sensor at an edge portion of the image detection unit of an imaging unit. If the X-ray sensor detects X-rays, this arrangement performs control to stop down (reduce) the aperture of the collimator until the X-ray sensor stops detecting X-rays. According to this reference, controlling an X-ray irradiation field can suppress X-ray irradiation outside the X-ray detection unit.

Furthermore, Japanese Patent Laid-Open No. 2001-292992 discloses a technique of bringing an X-ray irradiation field close to the center of an image detection unit by generating an X-ray image using the image detection unit and predicting an X-ray irradiation field based on the generated X-ray image. If the predicted irradiation field is offset from the center of the image detection unit, an instruction to change the position of an object is issued to the operator or control is performed to change the relative position between the X-ray irradiation unit and the imaging unit. With this operation, the technique disclosed in this reference can suppress X-ray irradiation outside the X-ray detection unit.

If, however, the relative position between the X-ray irradiation unit and the imaging unit greatly changes, the relative position detection accuracy may deteriorate. The relative position detection accuracy also deteriorates due to a change with time. For this reason, in the case of Japanese Patent Laid-Open No. 11-318877, if the relative position detection accuracy deteriorates due to such a cause, the accuracy of a predicted irradiation field deteriorates. In addition, if the relative angle between the X-ray irradiation unit and the imaging unit greatly changes and the incident angle of X-rays relative to the image detection unit becomes large, the accuracy of a predicted irradiation field further deteriorates. As a result, it can occur that X-ray irradiation outside the image detection unit cannot be reliably suppressed.

In the case of Japanese Patent Laid-Open No. 2001-104299, the detection accuracy of the X-ray sensor may deteriorate due to the influences of an object. If, for example, a region having a low X-ray transmittance is imaged, the X-ray sensor may not detect X-rays in spite of the fact that an irradiation field is located at an edge portion of the image detection unit. In this case, it is impossible to reliably suppress X-ray irradiation outside the image detection unit.

In the case of Japanese Patent Laid-Open No. 2001-292992 as well, when a region having a low X-ray transmittance such as a mediastinum or an abdominal region is imaged, the prediction accuracy of an irradiation field may deteriorate. That is, it can occur that X-ray irradiation outside the X-ray detection unit cannot be properly suppressed due to the influences of an object.

For this reason, a demand has arisen for an arrangement which can reliably suppress X-ray irradiation outside the image detection unit regardless of conditions at the time of imaging (e.g. one or more of a relative position, a relative angle, a change with time, and the influence of an imaging region).

SUMMARY OF THE INVENTION

The present invention has been made in consideration of the above problems.

An X-ray imaging apparatus comprising: a X-ray irradiation unit, including a generation unit which generates X-rays and a collimator including a stop to define a beam spread angle of the generated X-rays, configured to irradiate an object with X-rays at an arbitrary position and an arbitrary angle; a X-ray detection unit movably provided with an imaging unit including an image detection unit which generates an X-ray image by detecting X-rays transmitted through the object; a first calculation unit configured to calculate an irradiation field formed on the imaging unit by using a relative positional relationship between the generation unit and the imaging unit and an aperture value of the collimator; a second calculation unit configured to calculate the irradiation field formed on the imaging unit based on a dose of X-rays generated by the generation unit and an X-ray dose distribution detected by the image detection unit; and a decision unit configured to decide, as a predicted irradiation field, a region including one or both of irradiation fields respectively calculated by the first calculation unit and the second calculation unit, wherein an irradiation field formed on the imaging unit is controlled based on a predicted irradiation field decided by the decision unit.

According to the present invention, it is possible to reliably suppress X-ray irradiation outside an X-ray detection unit in an X-ray imaging apparatus.

Further features of the present invention will become apparent from the following description of exemplary embodiments (with reference to the attached drawings).

BRIEF DESCRIPTION OF THE DRAWINGS

The accompanying drawings, which are incorporated in and constitute a part of the specification, illustrate embodiments of the invention and, together with the description, serve to explain the principles of the invention.

FIGS. 7A, 7B, and 7C are views showing the certainty factors of predicted irradiation fields;

FIGS. 9A and 9B are views showing the certainty factors of predicted irradiation fields;

FIG. 10 is a flowchart showing a procedure for predicted irradiation field decision processing;

FIG. 13 is a view for explaining an embodiment of predicted irradiation field decision processing;

FIG. 16 is a view showing an example of a predicted irradiation field.

DESCRIPTION OF THE EMBODIMENTS

Embodiments of the present invention will now be described in detail in accordance with the accompanying drawings.

[First Embodiment]

<1. Overall Arrangement of X-Ray Imaging Apparatus>

Figure 1:
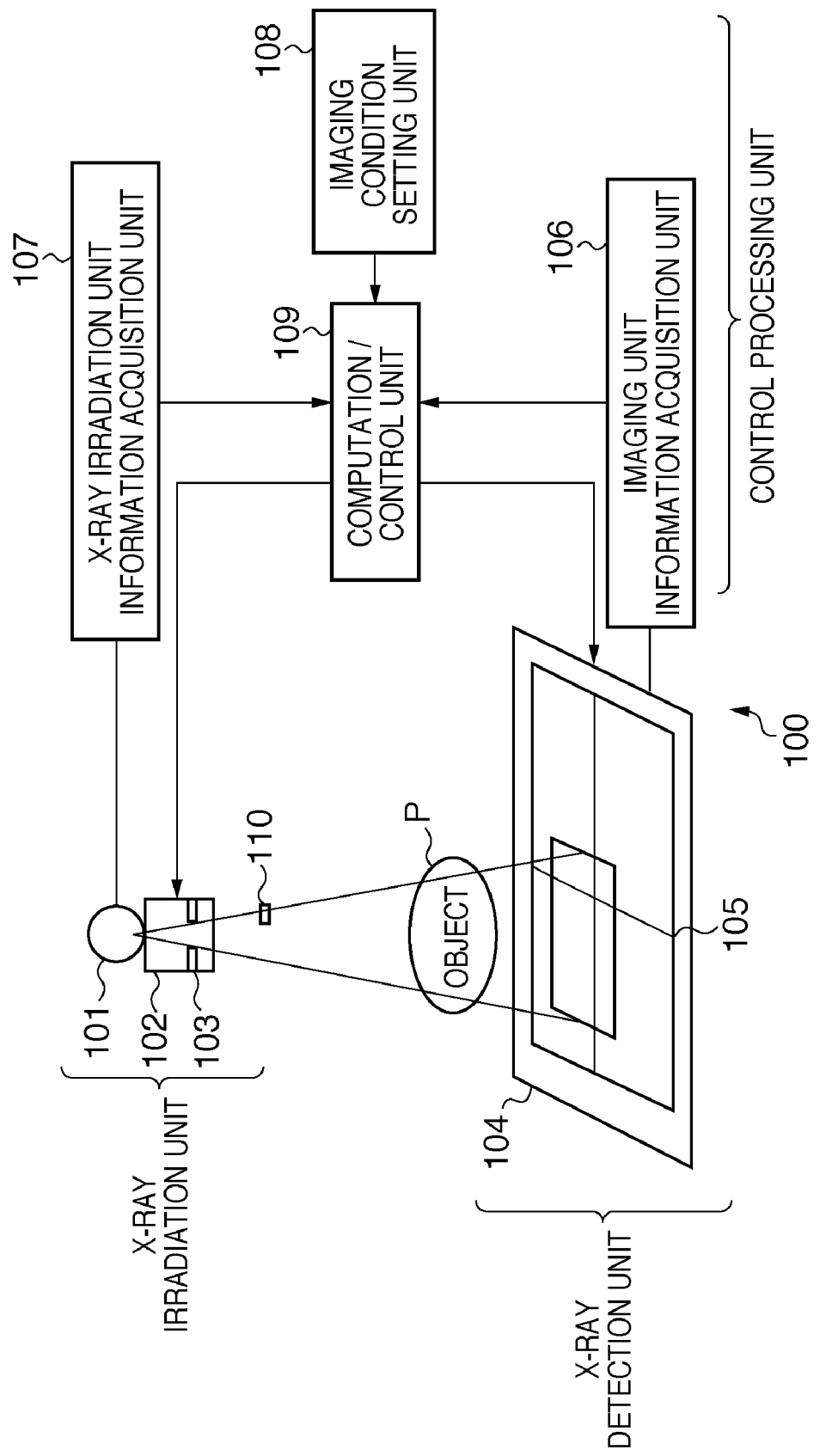
FIG. 1 is a view showing the overall arrangement of an X-ray imaging apparatus according to the first embodiment of the present invention.

FIG. 1 is a view showing the overall arrangement of an X-ray imaging apparatus 100. As shown in FIG. 1, the X-ray imaging apparatus 100 includes an X-ray irradiation unit which irradiates an object P with X-rays, an X-ray detection unit which detects X-rays transmitted through the object P, and a control processing unit which controls the X-ray irradiation unit and the X-ray detection unit.

The X-ray irradiation unit includes an X-ray generation unit (tube) 101 which generates X-rays, a collimator 102 which defines the spread angle of an X-ray beam generated by the X-ray generation unit 101, and a dosimeter 110. The X-ray irradiation unit further includes a driving unit (not shown), to move the X-ray irradiation unit (to change its position and angle, and the X-ray irradiation unit can irradiate the object P with X-rays at an arbitrary position and angle.

The collimator 102 incorporates a movable stop 103. The movable stop 103 is made of an X-ray blocking material (e.g., lead). Controlling the aperture value of the movable stop 103 will control the spread angle of X-rays. The movable stop 103 may be designed to allow a dial attached to the collimator 102 to control the aperture value. Alternatively, the movable stop 103 may be is designed to control the aperture value in accordance with an instruction from a computation/control unit 109 (to be described later).

The X-ray detection unit includes an imaging unit 104 and a driving unit (not shown) which allows the imaging unit 104 to move (to change its position and angle). The imaging unit 104 includes an image detection unit 105 which generates an X-ray image by converting X-rays transmitted through an object into an electrical signal. Preferably an arrangement of the arranging fine solid-state imaging elements in a two-dimensional lattice pattern forms the image detection unit 105.

The control processing unit includes an imaging unit information acquisition unit 106. The control processing unit acquires the X-ray image generated by the image detection unit 105 via the imaging unit information acquisition unit 106 and transmits the image to the computation/control unit 109. The control processing unit also acquires information concerning the imaging unit 104 (information concerning the position and angle) and transmits the information to the computation/control unit 109.

The control processing unit includes an X-ray irradiation unit information acquisition unit 107. The control processing unit acquires information concerning the X-ray irradiation unit (information concerning the position and angle of the X-ray generation unit (tube) 101 and the aperture of the movable stop 103) via the X-ray irradiation unit information acquisition unit 107 and transmits the information to the computation/control unit 109.

The control processing unit also includes an imaging condition setting unit 108. The imaging condition setting unit 108 accepts imaging conditions such as a frame rate, a tube voltage, and a tube current at the time of X-ray imaging from the operator, and sets them in the computation/control unit 109.

The control processing unit further includes the computation/control unit 109 that receives the information concerning the imaging unit 104 which is transmitted from the imaging unit information acquisition unit 106, the information concerning the X-ray irradiation unit which is transmitted from the X-ray irradiation unit information acquisition unit 107, and the imaging conditions set by the imaging condition setting unit 108. The computation/control unit 109 controls the X-ray irradiation unit and the X-ray detection unit based on these pieces of information.

<2. Functional Arrangement of Control Processing Unit>

Figure 2:
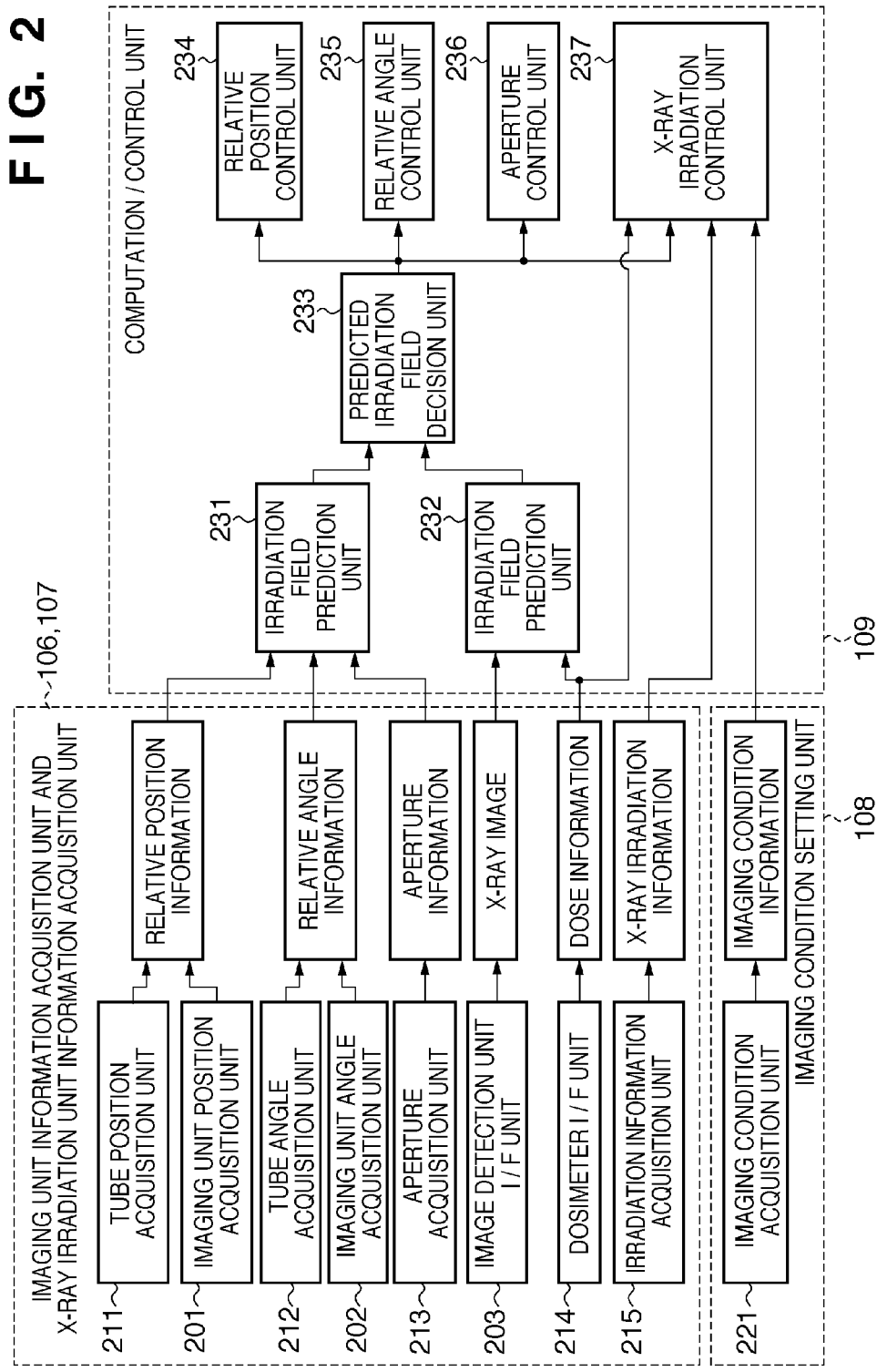
FIG. 2 is a block diagram showing the functional arrangement of the control processing unit of the X-ray imaging apparatus.

The functional arrangement of the control processing unit will be described next with reference to FIG. 2. As shown in FIG. 2, the imaging unit information acquisition unit 106 includes an imaging unit position acquisition unit 201, an imaging unit angle acquisition unit 202, and an image detection unit I/F unit 203.

The imaging unit position acquisition unit 201 detects the position of the imaging unit 104 and outputs imaging unit position information. The imaging unit angle acquisition unit 202 detects the tilt (angle) of the imaging unit 104 relative to a horizontal plane and outputs imaging unit angle information. The image detection unit I/F unit 203 outputs the X-ray image generated by the image detection unit 105.

The X-ray irradiation unit information acquisition unit 107 includes a tube position acquisition unit 211, a tube angle acquisition unit 212, an aperture acquisition unit 213, a dosimeter I/F unit 214, and an irradiation information acquisition unit 215.

The tube position acquisition unit 211 detects the position of the X-ray generation unit (tube) 101 and outputs tube position information. It is presumed that the orientation of the tube with respect to the collimator remains constant as the X-ray irradiation unit is moved as a whole. The tube angle acquisition unit 212 detects the angle of the tube relative to the vertical direction and outputs tube angle information. The aperture acquisition unit 213 detects the aperture of the movable stop 103 of the collimator 102 and outputs aperture information. The dosimeter I/F unit 214 outputs the X-ray dose measured by the dosimeter 110 as dose information. The irradiation information acquisition unit 215 detects and outputs X-ray irradiation information such as the tube voltage and tube current set when the X-ray generation unit (tube) 101 generates X-rays and an X-ray irradiation time per pulse in pulse fluoroscopy and irradiation intervals.

The imaging condition setting unit 108 includes an imaging condition acquisition unit 221. The imaging condition acquisition unit 221 acquires imaging conditions in X-ray imaging and outputs them as imaging condition information to the computation/control unit 109.

The computation/control unit 109 includes an irradiation field prediction unit 231 (a first calculation unit), an irradiation field prediction unit 232 (a second calculation unit), a predicted irradiation field decision (or determination) unit 233, a relative position control unit 234, a relative angle control unit 235, an aperture control unit 236, and an X-ray irradiation control unit 237.

The irradiation field prediction unit 231 of the computation/control unit 109 receives, as relative position information, the tube position information output from the tube position acquisition unit 211 and the imaging unit position information output from the imaging unit position acquisition unit 201. The irradiation field prediction unit 231 of the computation/control unit 109 receives, as relative angle information, the tube angle information output from the tube angle acquisition unit 212 and the imaging unit angle information output from the imaging unit angle acquisition unit 202. That is, the irradiation field prediction unit 231 receives information associated with the relative positional relationship between the X-ray generation unit 101 and the imaging unit 104. The information associated with the relative positional relationship may comprise the position information and/or the angle information relating to the X-ray generation unit and/or the imaging unit. For example, the imaging unit may be fixed in position whilst the X-ray generation unit is adjustable in either position and/or angle with respect to the imaging unit. In another example both the imaging unit and X-ray generation unit may be fixed such that they cannot be adjusted in angle but can be adjusted in position. In the present embodiment the position and angle of the X-ray generation unit and the imaging unit can be adjusted. Thus in the present embodiment the information associated with the relative positional relationship between the X-ray generation unit and the imaging unit comprises tube position information, imaging unit position information, tube angle information and imaging unit angle information.

The irradiation field prediction unit 232 and X-ray irradiation control unit 237 of the computation/control unit 109 receive the aperture information output from the aperture acquisition unit 213. The irradiation field prediction unit 232 of the computation/control unit 109 receives the dose information detected by the dosimeter 110 and output via the dosimeter I/F unit 214. The X-ray irradiation control unit 237 receives the X-ray irradiation information detected by the irradiation information acquisition unit 215. In addition, the X-ray irradiation control unit 237 receives the imaging condition information output from the imaging condition acquisition unit 221.

The irradiation field prediction unit 231 predicts the irradiation field formed on the imaging unit 104 by calculation based on the input relative position information, relative angle information, and aperture information. Meanwhile, the irradiation field prediction unit 232 predicts the irradiation field formed on the imaging unit 104 by calculation based on the input X-ray image (also known as a dose distribution) obtained from the image detection unit 105 and dose information.

The predicted irradiation field decision unit 233 decides (or determines) a final predicted irradiation field based on the irradiation field predicted by the irradiation field prediction unit 231 and the irradiation field predicted by the irradiation field prediction unit 232. The relative position control unit 234, the relative angle control unit 235, and the aperture control unit 236 control the irradiation field based on the predicted irradiation field finally decided (or determined) by the predicted irradiation field decision unit 233.

More specifically, the relative position control unit 234 controls the position of the X-ray generation unit (tube) 101 and the position of the imaging unit 104. The relative angle control unit 235 controls the angle of the X-ray generation unit (tube) 101 and the angle of the imaging unit 104. The aperture control unit 236 further controls the aperture value of the movable stop 103 of the collimator 102. This will suppress X-ray irradiation outside the X-ray detection unit.

The X-ray irradiation control unit 237 controls the dose of X-rays generated by the X-ray generation unit 101 based on the input dose information, X-ray irradiation information, and imaging condition information. Upon determining, based on the decided predicted irradiation field, that X-rays will be applied outside the X-ray detection unit, the X-ray irradiation control unit 237 performs control to stop X-ray irradiation.

<3. Procedure for X-Ray Imaging Processing>

Figure 3:
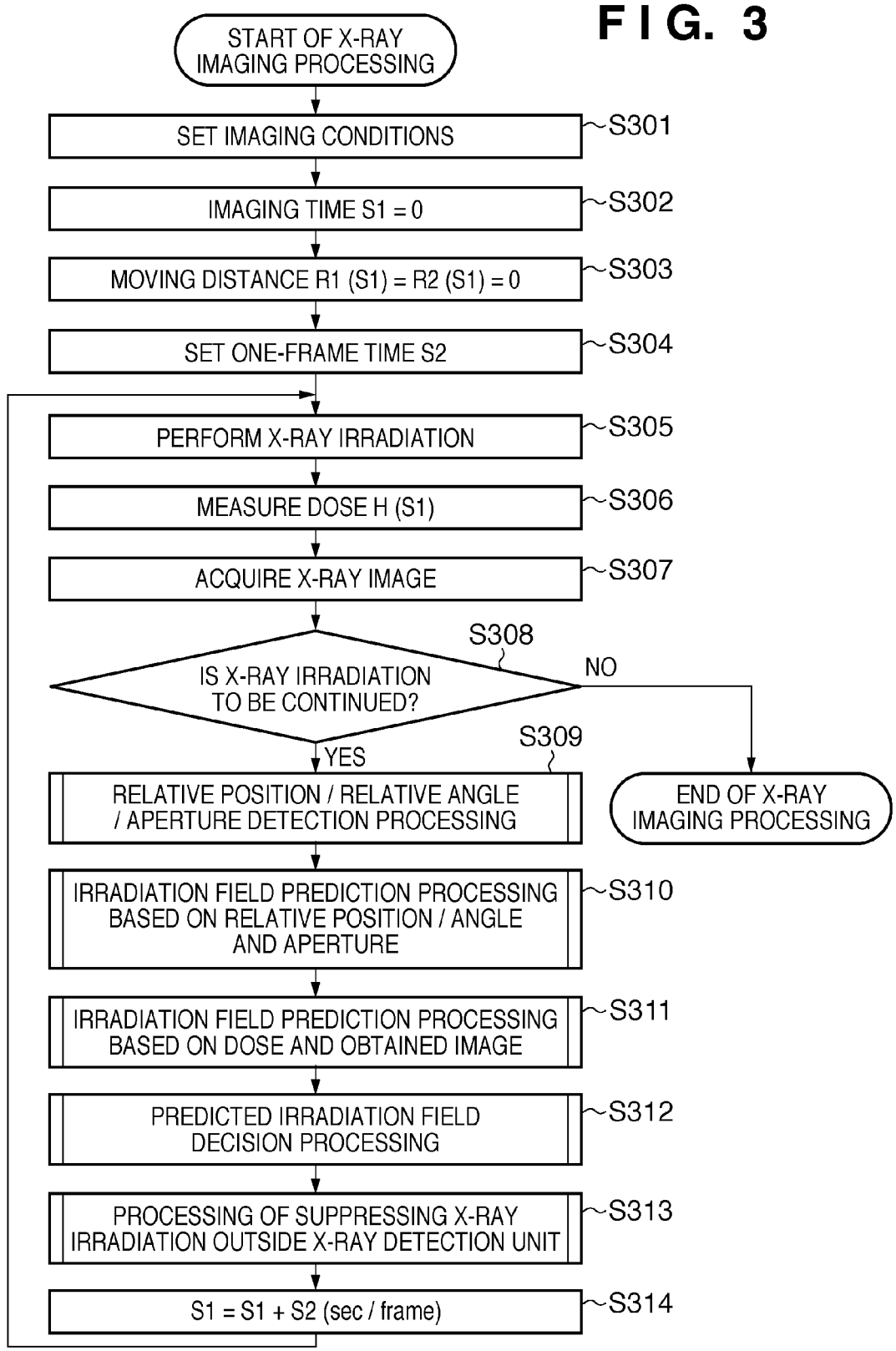
FIG. 3 is a flowchart showing a procedure for X-ray imaging processing in the X-ray imaging apparatus.

A procedure for X-ray imaging processing in the X-ray imaging apparatus 100 will be described next with reference to the flowchart shown in FIG. 3. Referring to FIG. 3, a variable S1 indicates the X-ray irradiation time (imaging time) from the start of X-ray imaging processing. In addition, variables R1(S1) and R2(S1) respectively indicate the sum totals of the moving distances of the X-ray generation unit (tube) 101 and imaging unit 104 in the interval between the instant X-ray imaging processing starts and the instant the time S1 elapses. Furthermore, a variable S2 indicates a time interval in which a one-frame X-ray image is obtained; and a variable H(S1), the dose applied to the object in a one-frame X-ray image obtained in the interval between the instant X-ray imaging processing starts and the instant the time S1 elapses.

When the operator inputs imaging conditions for imaging an object, such as a frame rate and a tube voltage, the imaging condition setting unit 108 accepts them and sets the imaging conditions in the computation/control unit 109 in step S301.

In step S302, the variable S1 is set to the initial value 0. In step S303, each of the variables R1(S1) and R2(S1) are set to the initial value 0 is set to each of the variables R1(S1) and R2(S1).

In step S304, the variable S2 indicating the interval in which a one-frame X-ray image is obtained is set based on the frame rate set in step S301.

In step S305, the X-ray irradiation unit irradiates the object with X-rays in accordance with the imaging conditions set in step S301. In step S306, the dosimeter 110 attached to the X-ray irradiation unit measures the dose H(S1) applied to the object during imaging to obtain one frame.

In step S307, the image detection unit 105 generates an X-ray image based on the X-rays transmitted through the object. In step S308, the operator determines whether to continue to irradiate the object with X-rays. If the operator determines to stop X-ray irradiation, the apparatus terminates the X-ray imaging processing. If the operator determines to continue X-ray irradiation, the process advances to step S309. In step S309, the apparatus detects the positions and angles of the X-ray generation unit (tube) 101 and imaging unit 104 and the aperture of the movable stop 103 of the collimator 102. Position/angle/aperture detection processing will be described in detail later.

In step S310, the irradiation field prediction unit 231 predicts an X-ray irradiation field based on the positions and angles of the X-ray generation unit (tube) 101 and imaging unit 104 and the aperture of the movable stop 103 of the collimator 102 which are detected in step S309. The irradiation field prediction unit 231 further calculates the certainty factor of the predicted irradiation field. Note that irradiation field prediction processing based on the positions, angles, and aperture will be described in detail later.

In step S311, the irradiation field prediction unit 232 predicts an X-ray irradiation field based on the dose H(S1) applied to the object during imaging to obtain a one-frame X-ray image, which is measured in step S306, and the X-ray image generated in step S307. The irradiation field prediction unit 232 further calculates the certainty factor of the predicted irradiation field. Note that irradiation field prediction processing based on the dose and X-ray image will be described in detail later.

In step S312, the predicted irradiation field decision unit 233 decides (or determines) a final predicted irradiation field based on the irradiation field predicted in step S310 and the irradiation field predicted in step S311. Note that predicted irradiation field decision (or determination) processing will be described in detail later.

In step S313, this apparatus determines whether the predicted irradiation field decided in step S312 is close to the boundary of the image detection unit 105. Upon determining that the decided predicted irradiation field is close to the boundary of the image detection unit 105, the apparatus controls at least one of the relative position control unit 234, the relative angle control unit 235, and the aperture control unit 236 so as to suppress X-ray irradiation outside the image detection unit 105. More specifically, the apparatus controls the relative position between the X-ray generation unit (tube) 101 and the imaging unit 104, the relative angle between them, and the aperture of the movable stop 103 of the collimator 102. Alternatively, the X-ray irradiation control unit 237 performs control to stop X-ray irradiation by the X-ray irradiation unit. If the apparatus determines in step S313 that the decided predicted irradiation field is far from the boundary of the image detection unit 105 (so the decided predicted irradiation field is comfortably within the image detection unit 105), the process directly advances to step S314.

In step S314, the X-ray irradiation time S1 from the start of X-ray imaging is updated by adding the interval S2 in which a one-frame X-ray image is obtained to the X-ray irradiation time S1 from the start of X-ray imaging processing. The process then returns to step S305.

<4. Position/Angle/Aperture Detection Processing>

A procedure for position/angle/aperture detection processing will be described next with reference to the flowchart of FIG. 4.

In step S401, the tube position acquisition unit 211 acquires pieces of three-dimensional position information X1(S1), Y1(S1), and Z1(S1) of the X-ray generation unit (tube) 101. The imaging unit position acquisition unit 201 acquires pieces of three-dimensional position information X2(S1), Y2(S1), and Z2(S1) of the imaging unit 104.

Figure 5:
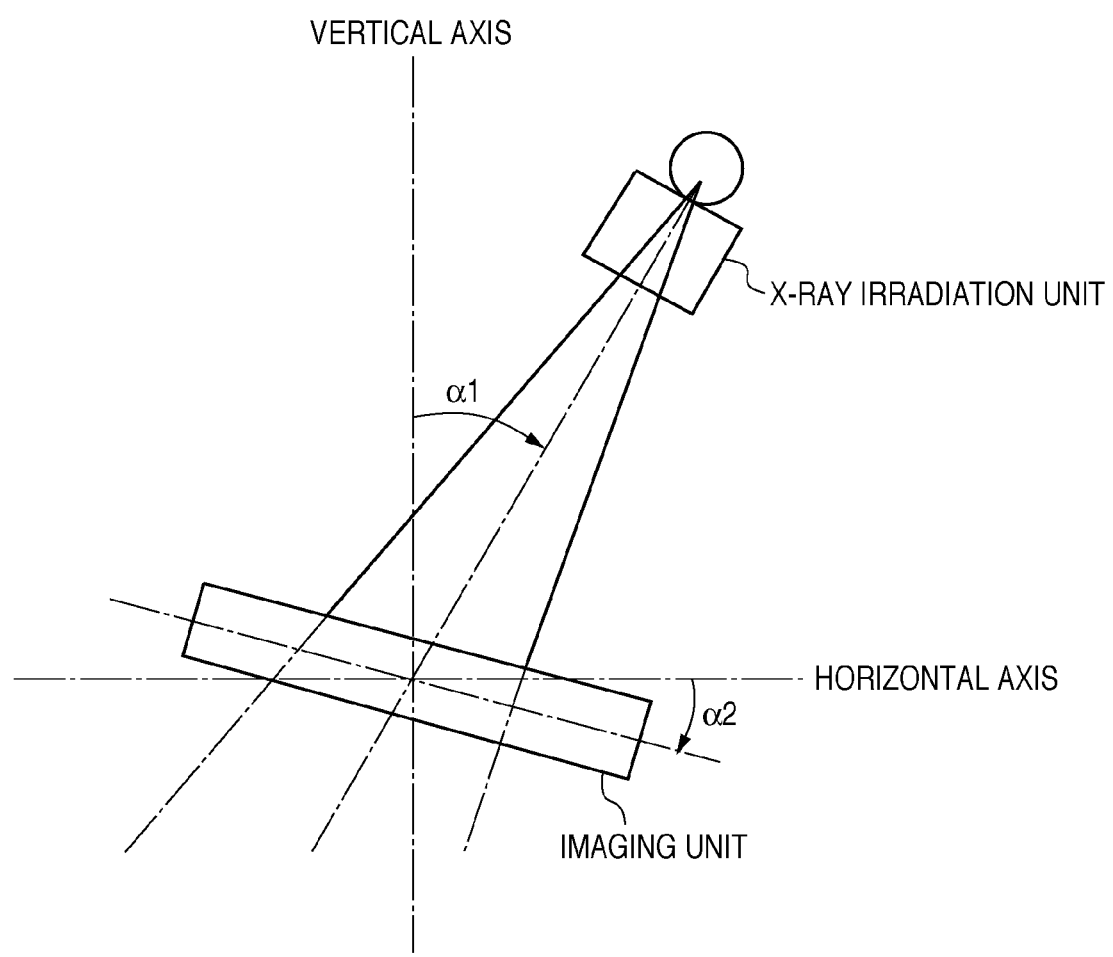
FIG. 5 is a view showing the positional relationship between an X-ray irradiation unit and an imaging unit.

In step S402, the tube angle acquisition unit 212 acquires an angle $\alpha 1$ of the X-ray generation unit (tube) 101 relative to the vertical direction. The imaging unit angle acquisition unit 202 acquires an angle $\alpha 2$ of the imaging unit 104 relative to the horizontal direction. Note that FIG. 5 shows the relationship between the angle $\alpha 1$ relative to the vertical direction and the angle $\alpha 2$ relative to the horizontal direction.

In step S403, this apparatus calculates relative positions X(S1), Y(S1), and Z(S1) between the X-ray generation unit (tube) 101 and the imaging unit 104 and a relative angle $\alpha$(S1) between them. The relative positions X(S1), Y(S1), and Z(S1) and the relative angle $\alpha$(S1) are calculated based on the position and angle differences between the X-ray generation unit (tube) 101 and the imaging unit 104 which are acquired in steps S401 and S402.

In step S404, the aperture acquisition unit 213 acquires the aperture of the movable stop 103 of the collimator 102 in two directions to obtain two aperture values L1(S1) and L2(S1). In step S405, the apparatus sets the values of pieces of position information X1(−S2), Y1(−S2), Z1(−S2), X2(−S2), Y2(−S2), and Z2(−S2) to calculate the moving distances of the X-ray generation unit (tube) 101 and imaging unit 104 when S1=0.

In step S406, this apparatus calculates the moving distance R1(S1) of the X-ray generation unit (tube) 101 by integrating the distance between the position of the X-ray generation unit (tube) 101 at the time of imaging to obtain the previous frame and the current position for each imaging frame. In step S407, the apparatus calculates the moving distance R2(S1) of the imaging unit 104 by the same method as in step S406.

In step S408, this apparatus calculates the sum totals of the moving distances of the X-ray generation unit (tube) 101 and imaging unit 104 from the start of X-ray imaging processing by adding the moving distances of the X-ray generation unit (tube) 101 and imaging unit 104 which are calculated in steps S406 and S407.

With the above processing, this apparatus calculates the relative position and relative angle between the X-ray generation unit (tube) 101 and the imaging unit 104, their moving distances, and the aperture of the collimator.

<5. Procedure for Irradiation Field Prediction Processing Based on Relative Position/Angle and Aperture>

Figure 6:
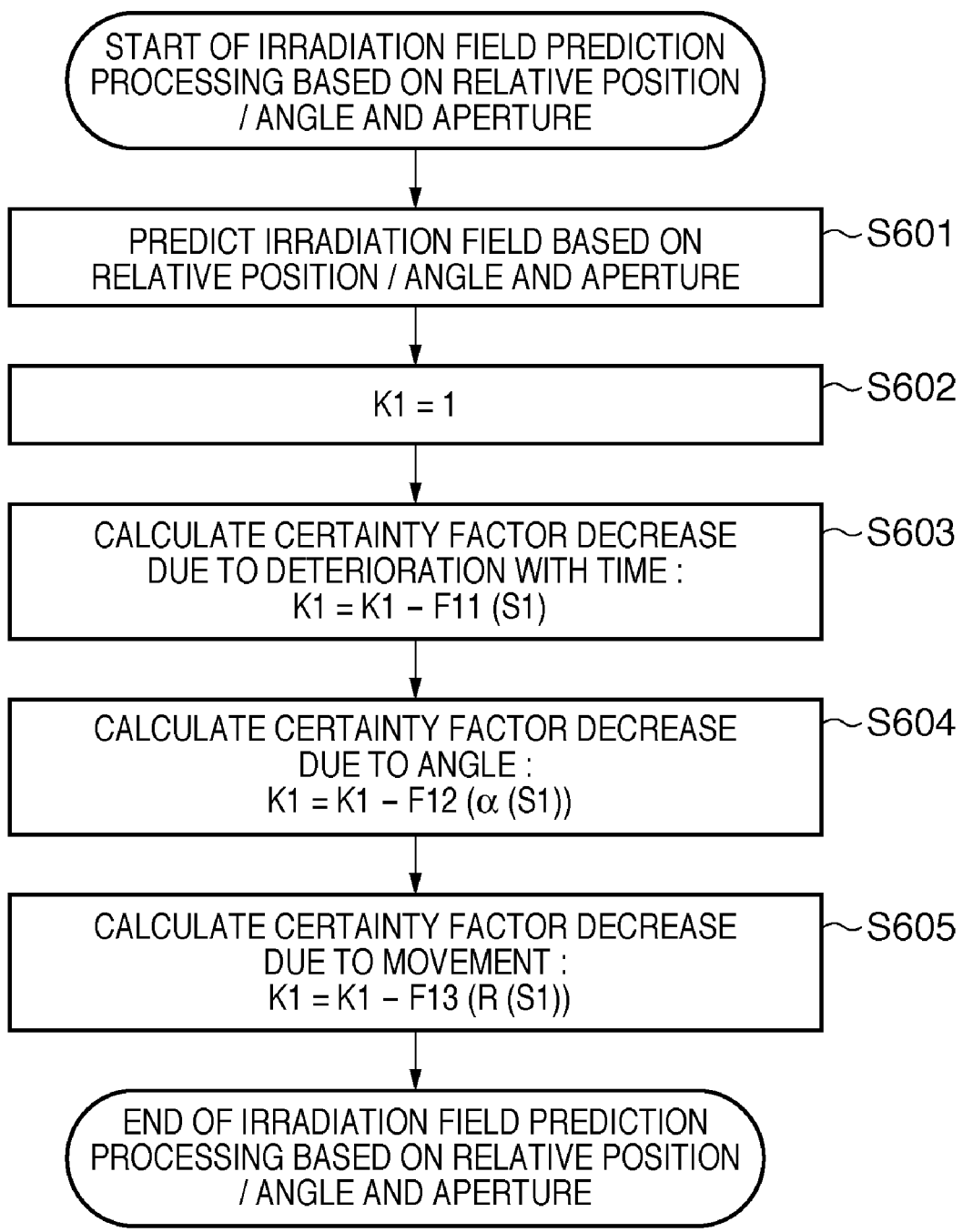
FIG. 6 is a flowchart showing a procedure for irradiation field prediction processing.

A procedure for irradiation field prediction processing performed by the irradiation field prediction unit 231 based on a relative position/angle and aperture will be described next with reference to the flowchart of FIG. 6.

Figure 4:
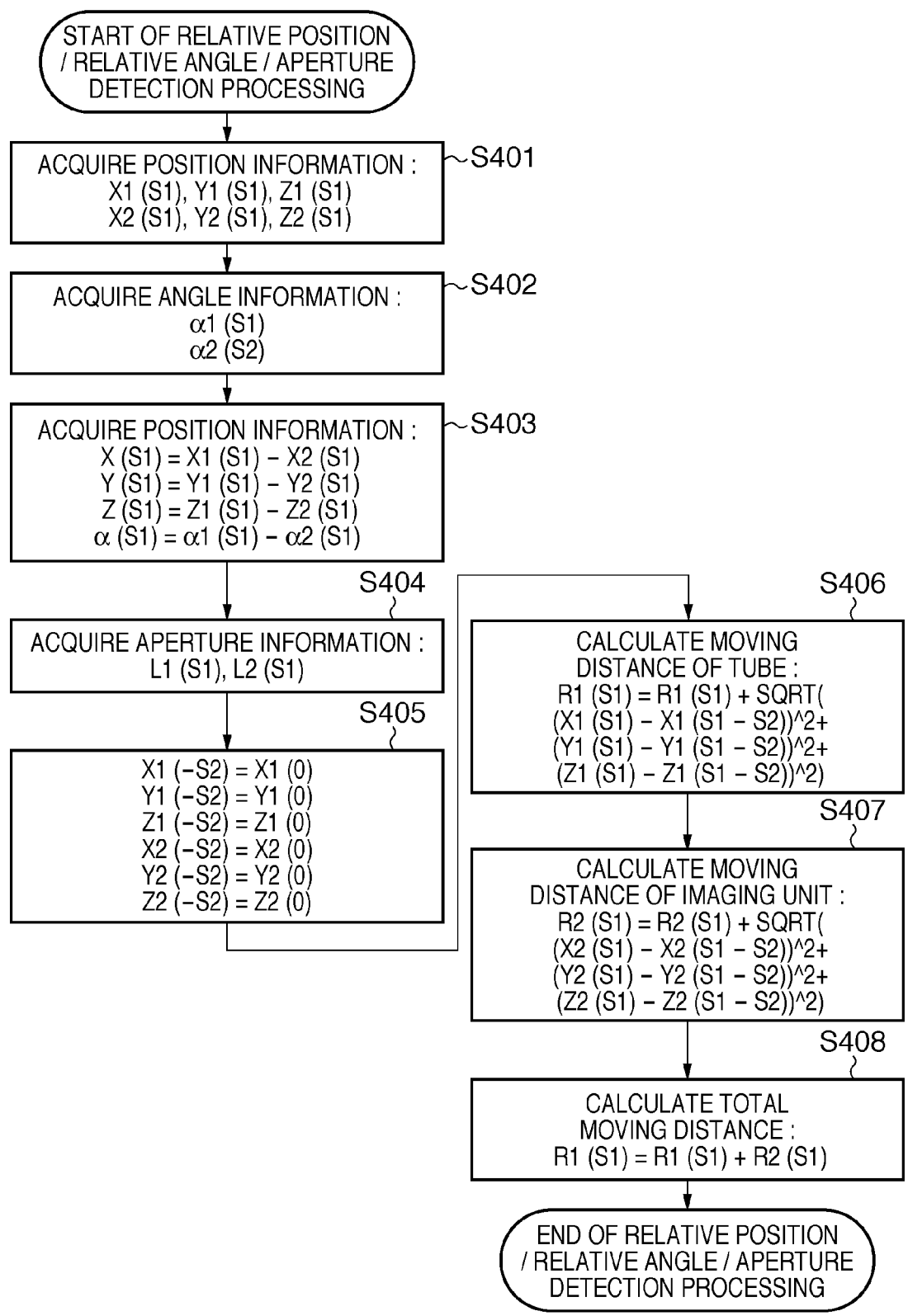
FIG. 4 is a flowchart showing a procedure for relative position/relative angle/aperture detection processing.

In step S601, the irradiation field prediction unit 231 predicts the irradiation field in which X-rays are applied on the imaging unit 104, based on the relative position and relative angle between the X-ray generation unit (tube) 101 and the imaging unit 104 and the aperture of the collimator which are detected by executing the flowchart shown in FIG. 4. An X-ray irradiation field can be geometrically predicted based on the relative position, relative angle, and collimator aperture information.

In step S602, the irradiation field prediction unit 231 sets the initial value 1 to a certainty factor K1 of the irradiation field predicted in step S601.

In step S603, the irradiation field prediction unit 231 calculates a certainty factor decrease due to a deterioration in relative position detection accuracy with time. F11(S1) is a function representing the relationship between the elapsed time S1 from the start of X-ray imaging processing and a certainty factor decrease due to a deterioration in relative position detection accuracy with time. FIG. 7A shows the relationship between S1 and F11(S1) by illustrating the values of the certainty factor decrease at particular (approximate) values of S1. In step S603, the irradiation field prediction unit 231 calculates a certainty factor decrease accompanying a deterioration with time by subtracting the value of F11(S1) from the certainty factor K1. The value of F11(S1) may be obtained from a table, such as shown in FIG. 7A, stored in advance.

In step S604, the irradiation field prediction unit 231 calculates a certainty factor decrease due to a large X-ray incident angle relative to the image detection unit 105 of the X-ray detection unit. F12($\alpha$(S1)) is a function representing a certainty factor decrease when the irradiation axis of X-rays forms the angle $\alpha$(S1) with the imaging unit 104. FIG. 7B shows the relationship between the relative angle $\alpha$(S1) and the certainty factor decrease function F12($\alpha$(S1)).

In step S604, the irradiation field prediction unit 231 calculates a certainty factor decrease due to a large X-ray incident angle by subtracting the value of F12(S1) from the certainty factor K1 obtained in step S603. The value of F12 (S1) may be obtained from a table, such as shown in FIG. 7B, stored in advance.

In step S605, the irradiation field prediction unit 231 calculates a certainty factor decrease due to a large change in the relative position between the X-ray generation unit (tube) 101 and the imaging unit 104. F13(R(S1)) is a function representing a certainty factor decrease due to the movement of the X-ray generation unit (tube) 101 and imaging unit 104 by a total moving distance R(S1). FIG. 7C shows the relationship between the total moving distance R(S1) and the certainty factor decrease function F13(R(S1)) due to movement.

In step S605, the irradiation field prediction unit 231 calculates a certainty factor decrease accompanying a large change in relative position by subtracting the value of F13(R (S1)) from the certainty factor K1 obtained in step S604. The value of F13(R(S1)) may be obtained from a table, such as shown in FIG. 7B, stored in advance.

With the above processing, the irradiation field prediction unit 231 can both predict an X-ray irradiation field based on the positions and angles of the X-ray generation unit (tube) 101 and imaging unit 104 and the aperture of the collimator and calculate the certainty factor of the predicted irradiation field.

<6. Procedure for Irradiation Field Prediction Processing Based on Dose and X-Ray Image>

Figure 8:
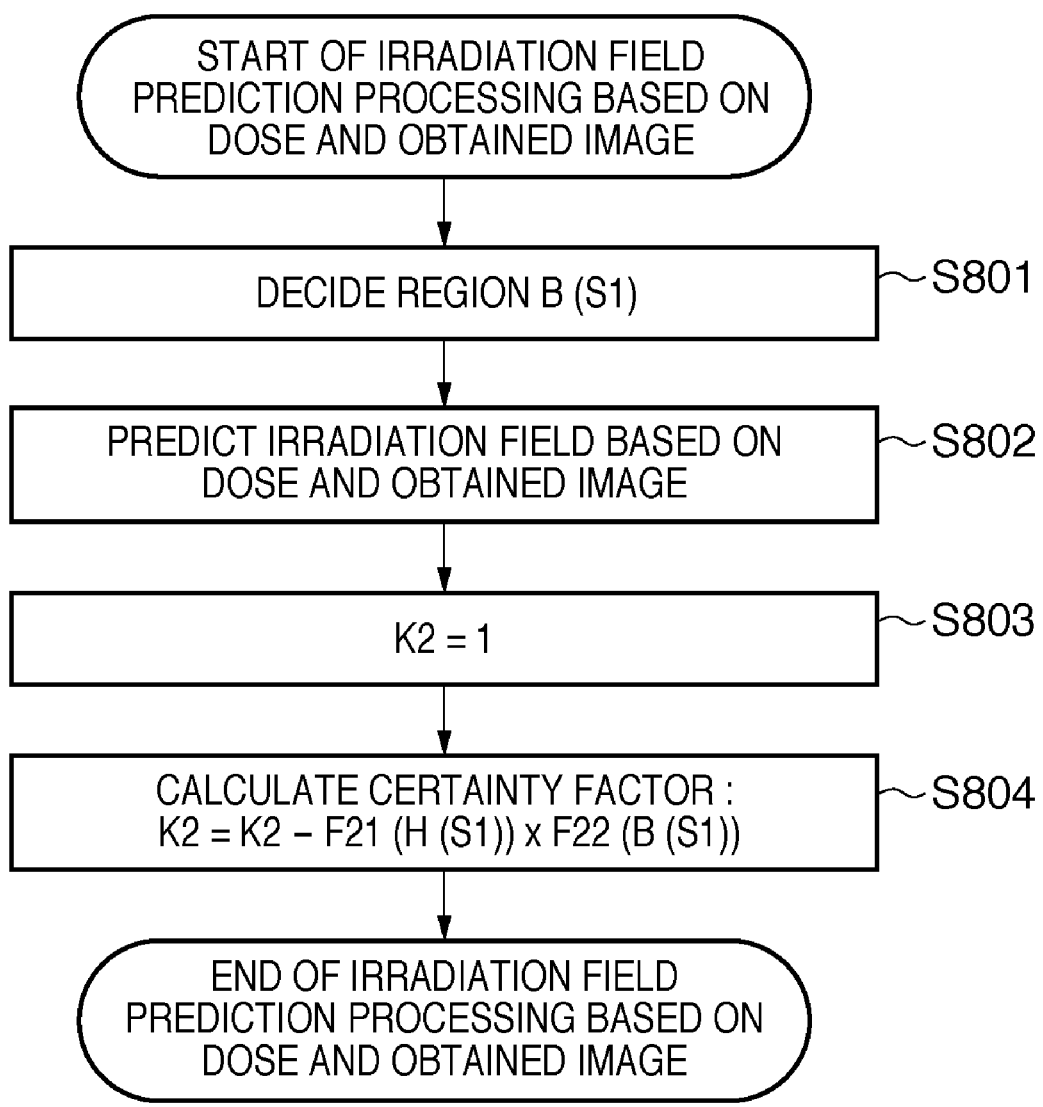
FIG. 8 is a flowchart showing a procedure for irradiation field prediction processing.

A procedure for irradiation field prediction processing performed by the irradiation field prediction unit 232 based on a dose and an X-ray image will be described next with reference to the flowchart of FIG. 8.

In step S801, the irradiation field prediction unit 232 estimates (or determines) a region B(S1) of an object based on the X-ray image generated by the image detection unit 105 in step S307 in FIG. 3. So, for example, the irradiation field prediction unit determines what particular region of the human body as the object has been irradiated with X-rays based on the obtained X-ray image. A known method is used as a method of estimating a region. Alternatively information indicating the region may be obtained from information input by an operator.

In step S802, the irradiation field prediction unit 232 estimates the X-ray irradiation field formed on the imaging unit 104 from the X-ray image generated by the image detection unit 105, the estimated region B(S1) of the object, and the dose applied to the object during imaging to obtain one frame, which is measured by the dosimeter 110. Note that a known technique is used as a method of estimating an X-ray irradiation field.

In step S803, the irradiation field prediction unit 232 sets the initial value 1 to a certainty factor K2 of the irradiation field predicted in step S802. In step S804, the irradiation field prediction unit 232 calculates the certainty factor of the irradiation field estimated in step S802 based on the dose H(S1) applied to the object during imaging to obtain one frame, which is measured in step S306, and the region information B(S1) of the X-ray image estimated in step S801.

F21(H(S1)) is a function representing an irradiation field prediction certainty factor decrease due to a small dose of X-rays applied to the object during imaging to obtain one frame. The irradiation field prediction certainty factor decreases as the dose decreases because as the dose decreases, the recognition accuracy of an irradiation field decreases due to the influence of X-ray dose noise.

F22(B(S1)) is a function representing an irradiation field prediction certainty factor decrease caused when a region having a low X-ray transmittance is imaged. FIGS. 9A and 9B respectively show the relationship between F21(F(S1)) and H(S1) (by illustrating the values of the certainty factor decrease at particular (approximate) values of the X-ray dose) and the relationship between F22(B(S1)) and B(S1) (by illustrating the values of the certainty factor decrease for particular regions). In step S804, the irradiation field prediction unit 232 calculates the certainty factor of the irradiation field predicted in step S802 by subtracting the product of the certainty factor decrease amount F21(H(S1)) based on the X-ray irradiation dose and the certainty factor decrease amount F22(B(S1)) due to the imaging region from the irradiation field prediction certainty factor K2.

With the above processing, it is possible to predict an X-ray irradiation field based on a dose and an X-ray image and calculate the certainty factor of a predicted irradiation field.

<7. Procedure for Predicted Irradiation Field Decision Processing>

A procedure for predicted irradiation field decision processing by the predicted irradiation field decision unit 233 will be described next with reference to FIG. 10.

In step S1001, the predicted irradiation field decision unit 233 calculates a difference |K1−K2| between the certainty factor K1 of the irradiation field predicted by the irradiation field prediction unit 231 and the certainty factor K2 of the irradiation field predicted by the irradiation field prediction unit 232. If the calculated difference is larger than a certainty factor difference threshold T1, the process advances to step S1002. Otherwise (if the difference is equal to or less than the certainty factor difference threshold), the process advances to step S1005.

In step S1002, the predicted irradiation field decision unit 233 compares the certainty factor K1 of the irradiation field predicted by the irradiation field prediction unit 231 with the certainty factor K2 of the irradiation field predicted by the irradiation field prediction unit 232. If the predicted irradiation field decision unit 233 determines in step S1002 that the certainty factor K1 is larger than the certainty factor K2, the process advances to step S1004. Otherwise, the process advances to step S1003.

In step S1003, the predicted irradiation field decision unit 233 decides the irradiation field predicted by the irradiation field prediction unit 232 as a final predicted irradiation field. In step S1004, the predicted irradiation field decision unit 233 decides the irradiation field predicted by the irradiation field prediction unit 231 as a final predicted irradiation field.

In step S1005, the predicted irradiation field decision unit 233 decides, as a final predicted irradiation field, a region including the irradiation field predicted by the irradiation field prediction unit 231 and the irradiation field predicted by the irradiation field prediction unit 232 or a wider region.

In this manner, if there is an apparent difference between the certainty factors of the X-ray irradiation fields predicted by two different techniques, the X-ray imaging apparatus according to this embodiment decides one of the predicted irradiation fields which has a larger certainty factor as a final predicted irradiation field. If the certainty factors of the X-ray irradiation fields predicted by two different techniques are almost equal to each other, the apparatus decides, as a final predicted irradiation field, a region including at least one of the two irradiation fields or a wider region.

<8. Example of Predicted Irradiation Field Decision Processing>

The first example of predicted irradiation field decision processing in the predicted irradiation field decision unit 233 will be described next.

Figures 11, 12:
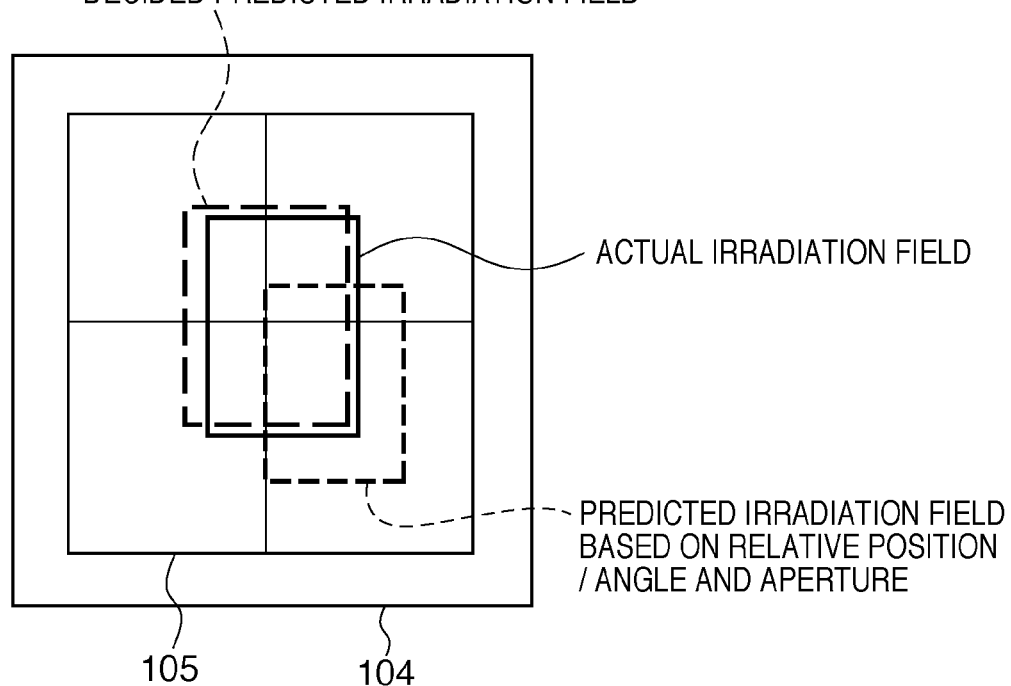
FIG. 11 is a view for explaining an embodiment of predicted irradiation field decision processing.
FIG. 12 is a view showing an example of a predicted irradiation field.

FIG. 11 is a table showing various variables set at the time of predicted irradiation field decision processing and the finally decided predicted irradiation field. In the case shown in FIG. 11, the elapsed time S1 from the start of X-ray imaging processing is five min, the relative angle α is 4°, the total moving distance R(S1) is 1 m, the dose at an imaging frame is 10 μR, and the imaging region is a pelvis region.

In this case, the certainty factor of the X-ray irradiation field predicted by the irradiation field prediction unit 231 is 0.68, and the certainty factor of the X-ray irradiation field predicted by the irradiation field prediction unit 232 is 0.92. As a final predicted irradiation field, the X-ray irradiation field predicted by the irradiation field prediction unit 232 is decided.

FIG. 12 shows irradiation fields for this example. As shown in FIG. 12, the irradiation field predicted by the irradiation field prediction unit 232 exhibits a higher certainty factor, and is a better approximation to the actual irradiation field. As a consequence, the irradiation field predicted by the irradiation field prediction unit 232 is decided (or determined) as a final predicted irradiation field.

The second example of predicted irradiation field decision processing by the predicted irradiation field decision unit 233 will be described next.

FIG. 13 is a table showing various variables set at the time of predicted irradiation field decision processing and the finally decided predicted irradiation field. In the case shown in FIG. 13, the elapsed time S1 from the start of X-ray imaging processing is 3 min, the relative angle α is 1°, the total moving distance R(S1) is 0.4 m, the dose at an imaging frame is 3 μR, and the imaging region is an abdominal region.

In this case, the certainty factor of the X-ray irradiation field predicted by the irradiation field prediction unit 231 is 0.9, and the certainty factor of the X-ray irradiation field predicted by the irradiation field prediction unit 232 is 0.5. As a consequence, the X-ray irradiation field predicted by the irradiation field prediction unit 231 is decided as a final predicted irradiation field.

<9. Processing of Suppressing X-Ray Irradiation outside X-Ray Detection Unit>

A procedure for processing of suppressing X-ray irradiation outside the X-ray detection unit based on the predicted irradiation field decided by the predicted irradiation field decision unit 233 will be described next with reference to FIG. 14.

Figure 14:
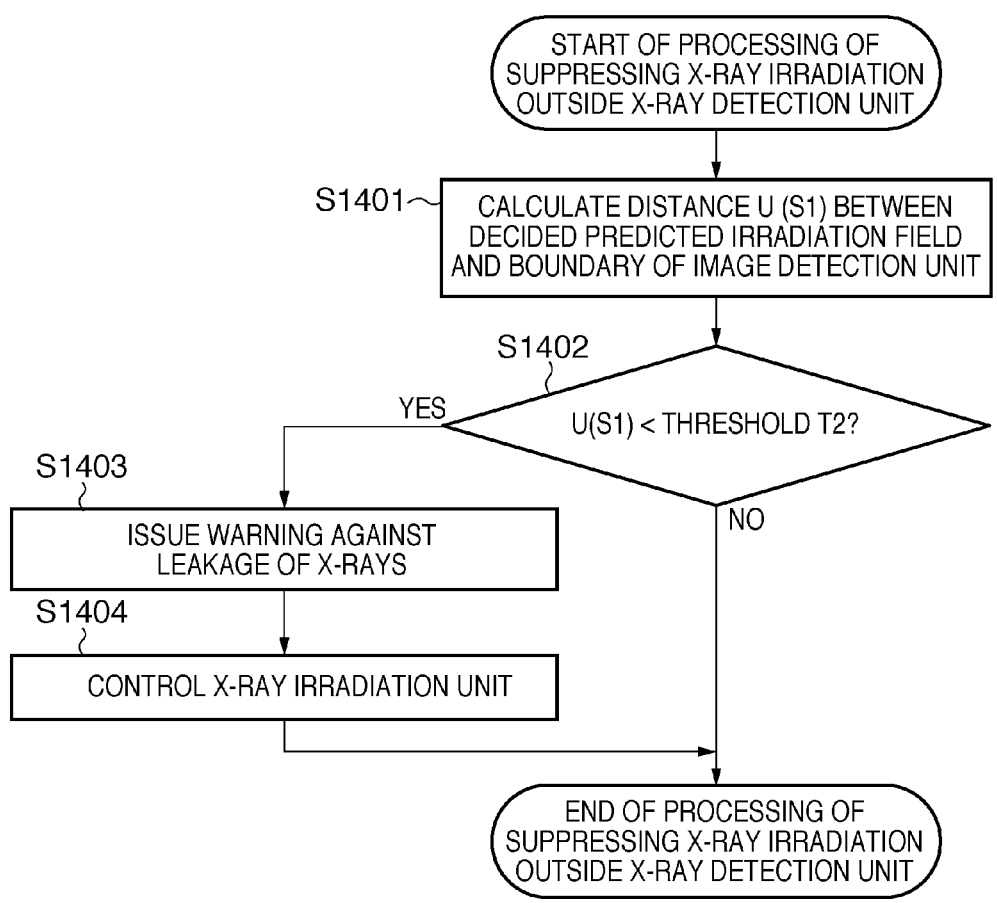
FIG. 14 is a flowchart showing a procedure for the processing of suppressing X-ray irradiation outside the X-ray detection unit.

When the predicted irradiation field decision unit 233 determines a predicted irradiation field, the processing of suppressing X-ray irradiation outside the X-ray detection unit shown in FIG. 14 starts.

In step S1401, this apparatus calculates a minimum distance U(S1) between an end (or edge) portion of a decided predicted irradiation field and the image detection unit 105. In step S1402, the apparatus compares the minimum distance U(S1) calculated in step S1401 with a distance threshold T2. If the apparatus determines in step S1402 that the minimum distance U(S1) is smaller than the distance threshold T2, the process advances to step S1403. If the minimum distance U(S1) is equal to or more than the distance threshold T2, the apparatus terminates the processing of suppressing X-ray irradiation outside X-ray detection unit.

In step S1403, this apparatus warns the operator that an end portion of the irradiation field is close to the boundary of the image detection unit 105. In step S1404, the apparatus controls the relative position/angle between the X-ray generation unit (tube) 101 and the imaging unit 104 or the aperture of the collimator to suppress X-ray irradiation outside the image detection unit 105. Alternatively, the apparatus performs control to stop X-ray irradiation.

With this operation, if it is determined that an end portion of a decided predicted irradiation field is close to the boundary of the image detection unit 105, it is possible to suppress X-ray irradiation outside the image detection unit 105.

As is clear from the above description, the X-ray imaging apparatus according to this embodiment calculates the certainty factors of the X-ray irradiation fields predicted by two different techniques. If there is an apparent difference between the respective certainty factors, a predicted irradiation field exhibiting a larger certainty factor is decided as a final predicted irradiation field.

If the respective certainty factors are almost equal to each other, the apparatus decides, as a final predicted irradiation field, a given region included in the two irradiation fields or a region including the given region and wider than it.

As a consequence, the X-ray imaging apparatus according to this embodiment can accurately predict an irradiation field regardless of conditions such as a relative position, a change with time, an incident angle, and the X-ray transmittance of an object. This makes it possible to reliably suppress X-ray irradiation outside the X-ray detection unit.

[Second Embodiment]

The first embodiment described above is configured to change the predicted irradiation field to be finally decided, based on the certainty factors of X-ray irradiation fields predicted by two different techniques. However, the present invention is not limited to the use of certainty factors.

The apparatus may be configured to decide, as a final predicted irradiation field, a given region including both the X-ray irradiation fields predicted by the two different techniques or a region including the given region and wider than it.

Figure 15:
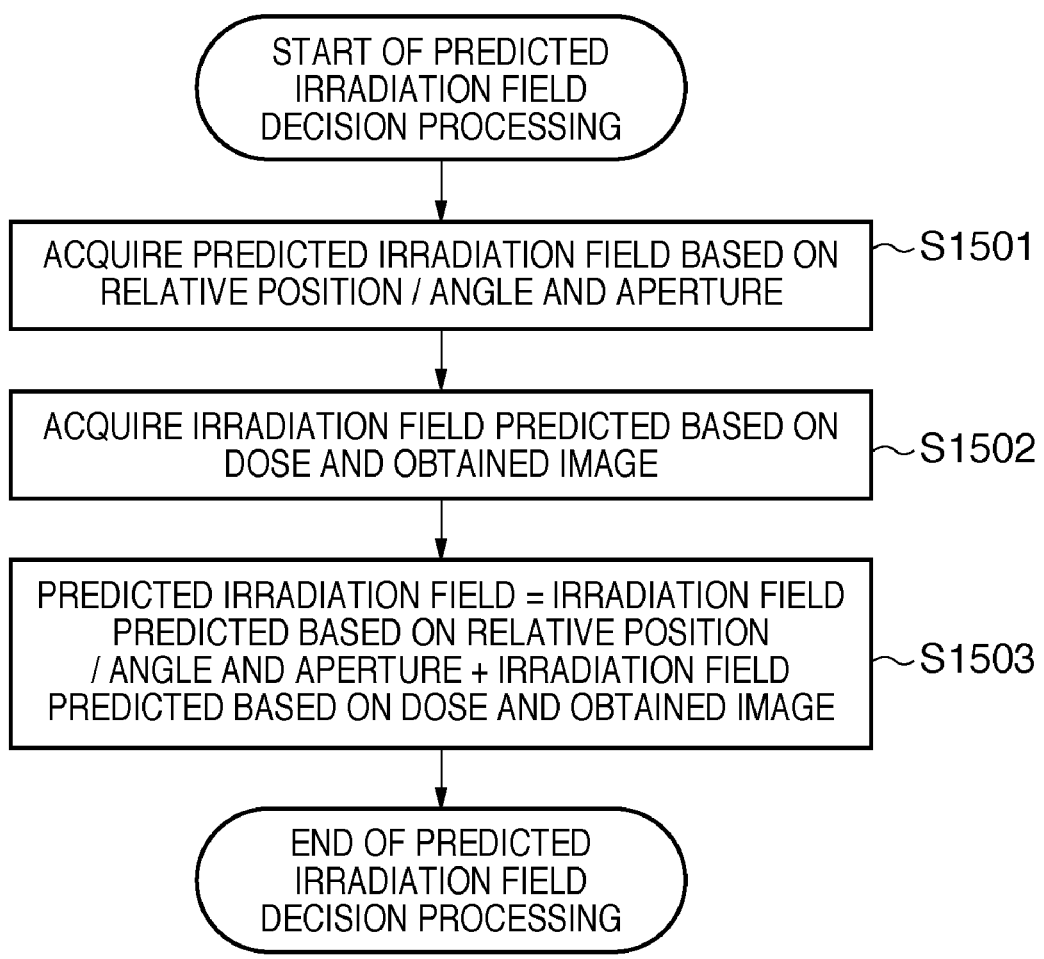
FIG. 15 is a flowchart showing a procedure for predicted irradiation field decision processing.

FIG. 15 is a flowchart showing a procedure for predicted irradiation field decision processing in an X-ray imaging apparatus according to this embodiment. As shown in FIG. 15, in step S1501, this apparatus acquires the irradiation field predicted by an irradiation field prediction unit 231. In step S1502, the apparatus acquires the irradiation field predicted by an irradiation field prediction unit 232.

In step S1503, this apparatus decides (or determines), as a final predicted irradiation field, a given region including both the irradiation field predicted by the irradiation field prediction unit 231 and the irradiation field predicted by the irradiation field prediction unit 232 or a region including the given region and wider than it.

FIG. 16 is a view showing an example of the predicted irradiation field decided by the predicted irradiation field decision unit of the X-ray imaging apparatus according to this embodiment.

As shown in FIG. 16, the finally decided predicted irradiation field is a rectangular region including the irradiation field predicted by the irradiation field prediction unit 231 and the irradiation field predicted by the irradiation field prediction unit 232. This rectangular region includes the actual irradiation field.

That is, in this embodiment, an actual irradiation field is reliably included in the finally decided predicted irradiation field 1604. This can reliably suppress X-ray irradiation outside the X-ray detection unit.

This arrangement is especially effective for a case in which a higher priority is assigned to the prevention of X-ray irradiation outside the image detection unit than to the degree of freedom in X-ray imaging.

[Other Embodiment]

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium). The invention may be embodied in such a program. The program may be carried on a carrier medium such as a computer readable storage medium or a transmission medium (signal).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-100373 filed Apr. 16, 2009, which is hereby incorporated by reference herein in its entirety.

What is claimed is:

1. An X-ray imaging apparatus comprising:
   an X-ray irradiation unit, including a generation unit which generates X-rays and a collimator including a stop to define a beam spread angle of the generated X-rays, configured to irradiate an object with X-rays at an arbitrary position and an arbitrary angle;
   an X-ray detection unit movably provided with an imaging unit including an image detection unit which generates an X-ray image by detecting X-rays transmitted through the object;
   a first calculation unit configured to calculate an irradiation field formed on said imaging unit by using a relative positional relationship between said generation unit and said imaging unit and an aperture value of said collimator;
   a second calculation unit configured to calculate the irradiation field formed on said imaging unit based on a dose of X-rays generated by said generation unit and an X-ray dose distribution detected by said image detection unit; and
   a decision unit configured to decide, as a predicted irradiation field, a region including one or both of irradiation fields respectively calculated by said first calculation unit and said second calculation unit,
   wherein an irradiation field formed on said imaging unit is controlled based on a predicted irradiation field decided by said decision unit.

2. The apparatus according to claim 1, wherein, if a difference between a certainty factor of an irradiation field calculated by said first calculation unit and a certainty factor of an irradiation field calculated by said second calculation unit is larger than a predetermined threshold, said decision unit decides an irradiation field exhibiting a higher certainty factor as the predicted irradiation field.

3. The apparatus according to claim 1, wherein, if a difference between a certainty factor of an irradiation field calculated by said first calculation unit and a certainty factor of an irradiation field calculated by said second calculation unit is not more than a predetermined threshold, said decision unit decides, as the predicted irradiation field, a region including the irradiation field calculated by said first calculation unit and the irradiation field calculated by said second calculation unit.

4. The apparatus according to claim 1, wherein said decision unit decides, as the predicted irradiation field, a region including an irradiation field calculated by said first calculation unit and an irradiation field calculated by said second calculation unit.

5. The apparatus according to claim 1, wherein a certainty factor of an irradiation field calculated by said first calculation unit is calculated by using a variable set in advance based on a time from start of X-ray irradiation by said X-ray irradiation unit and a relative positional relationship between said generation unit and said imaging unit.

6. The apparatus according to claim 1, wherein a certainty factor of an irradiation field calculated by said second calculation unit is calculated by using a variable set in advance based on a dose of X-rays generated by said generation unit and a region of an object irradiated with the X-rays.

7. A control method in an X-ray imaging apparatus comprising an X-ray irradiation unit, including a generation unit which generates X-rays and a collimator including a stop to define a beam spread angle of the generated X-rays, for irradiating an object with X-rays at an arbitrary position and an arbitrary angle, and an X-ray detection unit movably provided with an imaging unit including an image detection unit which generates an X-ray image by detecting X-rays transmitted through the object, comprising:
   a first calculation step of causing a first calculation unit to calculate an irradiation field formed on the imaging unit by using a relative positional relationship between the generation unit and the imaging unit and an aperture value of the collimator;
   a second calculation step of causing a second calculation unit to calculate the irradiation field formed on the imaging unit based on a dose of X-rays generated by the generation unit and an X-ray dose distribution detected by the image detection unit; and
   a decision step of causing a decision unit to decide, as a predicted irradiation field, a region including one or both of irradiation fields respectively calculated in said first calculation step and said second calculation step,
   wherein an irradiation field formed on the imaging unit is controlled based on a predicted irradiation field decided in said decision step.

8. A non-transitory computer-readable storage medium which stores a program for causing a computer to execute a control method defined in claim 7.

* * * * *